United States Patent

Arnegger et al.

[11] Patent Number: 5,569,257
[45] Date of Patent: Oct. 29, 1996

[54] SAW BLADE FOR PARTING CUTS MADE IN AN OSCILLATING OR ROTARY MANNER

[75] Inventors: Richard E. Arnegger, Uerikon, Switzerland; Antonius G. M. Gunnewijk, Feldbach, Netherlands; Thomas Maurer, Zürich, Switzerland

[73] Assignee: Ricana AG, Uerikon, Switzerland

[21] Appl. No.: 284,342

[22] Filed: Aug. 2, 1994

[30] Foreign Application Priority Data

Aug. 3, 1993 [CH] Switzerland ............... 02327/93

[51] Int. Cl.⁶ .................................... A61B 17/14
[52] U.S. Cl. .................................. 606/82; 30/350
[58] Field of Search ............... 606/82, 167, 170, 606/176–179; 30/350

[56] References Cited

U.S. PATENT DOCUMENTS

| 1,967,020 | 7/1934 | Canfield . | |
|---|---|---|---|
| 3,802,078 | 4/1974 | Denes | 30/350 |
| 3,910,774 | 10/1975 | Krienke . | |
| 3,988,955 | 11/1976 | Engel et al. | 30/350 |
| 4,513,742 | 4/1985 | Arnegger | 30/350 |
| 4,584,999 | 4/1986 | Arnegger | 30/350 |
| 5,178,626 | 1/1993 | Pappas | 606/82 |

FOREIGN PATENT DOCUMENTS

| 382483 | 8/1990 | European Pat. Off. . |
| 1577984 | 2/1970 | Germany . |
| 2849760 | 6/1979 | Germany . |
| 3222339 | 1/1983 | Germany . |
| WO93/01751 | 2/1993 | WIPO . |

*Primary Examiner*—Michael Powell Buiz
*Assistant Examiner*—William Lewis
*Attorney, Agent, or Firm*—Walter C. Farley

[57] ABSTRACT

The saw blade has a non-cutting blade area (2), whose thickness D is smaller than the width of cut S of its cutting area (4). The non-cutting blade area (2) has on either side a thin surface coating (11) of a relatively soft and biologically neutral precious metal. This leads to much better cutting characteristics and to reduced friction. The saw blade is particularly suitable for bone surgery.

12 Claims, 3 Drawing Sheets

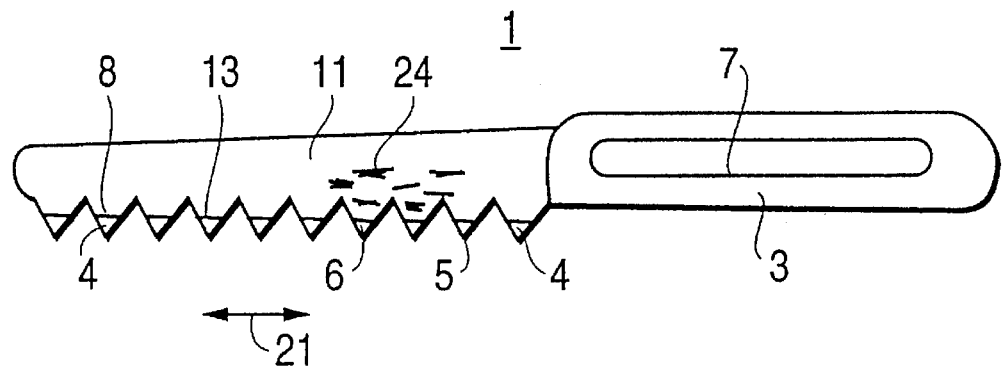
FIG. 1
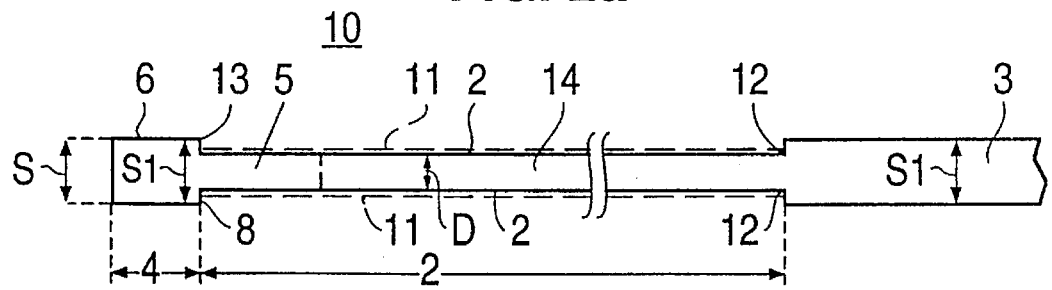
FIG. 2a
FIG. 2b
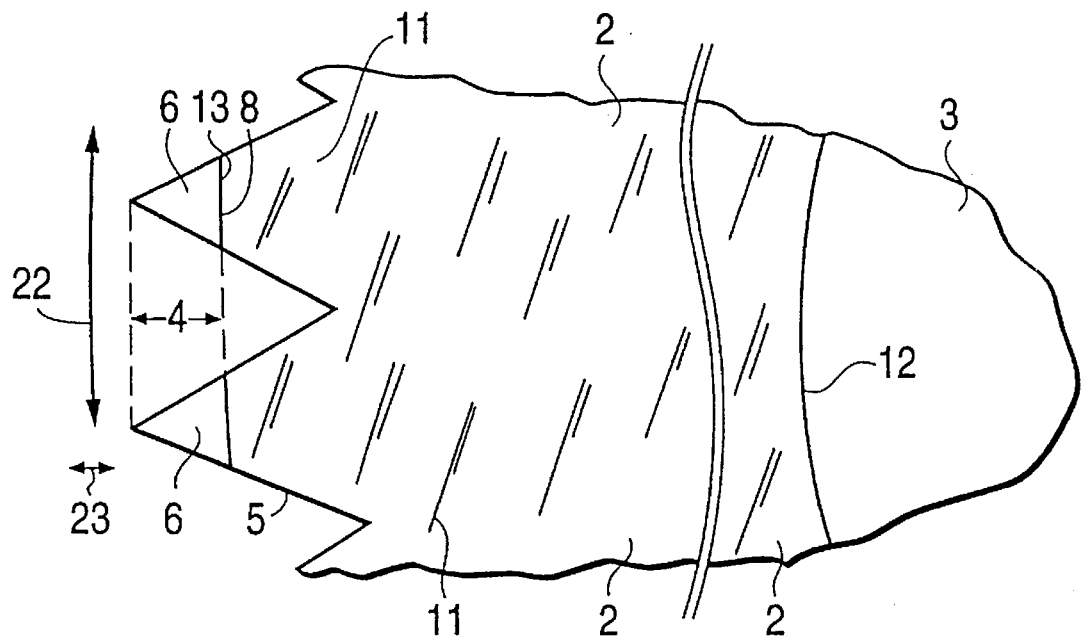

FIG. 3
FIG. 4
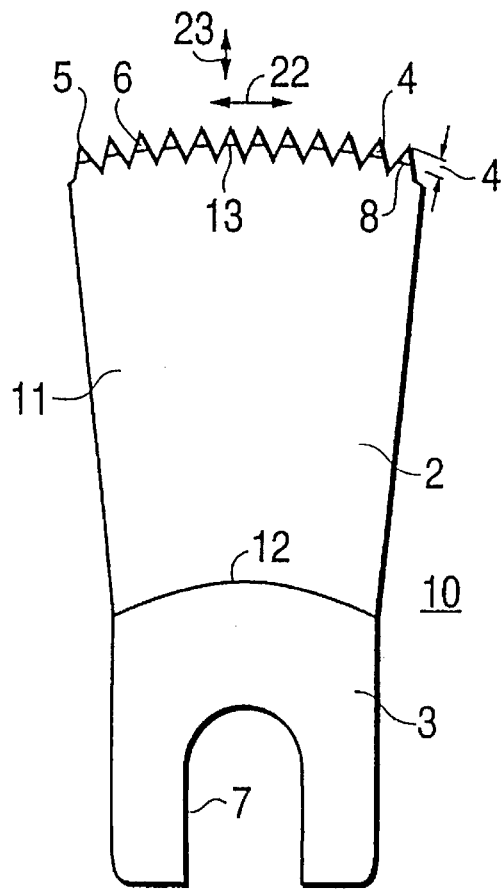
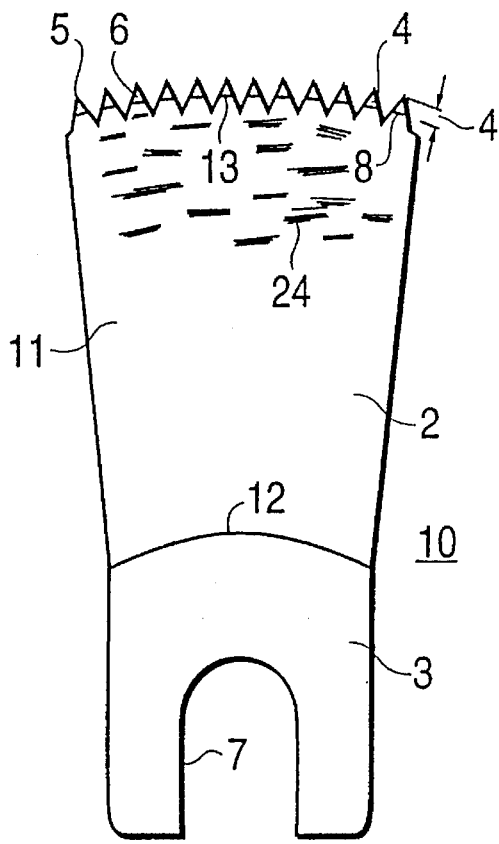
FIG. 5
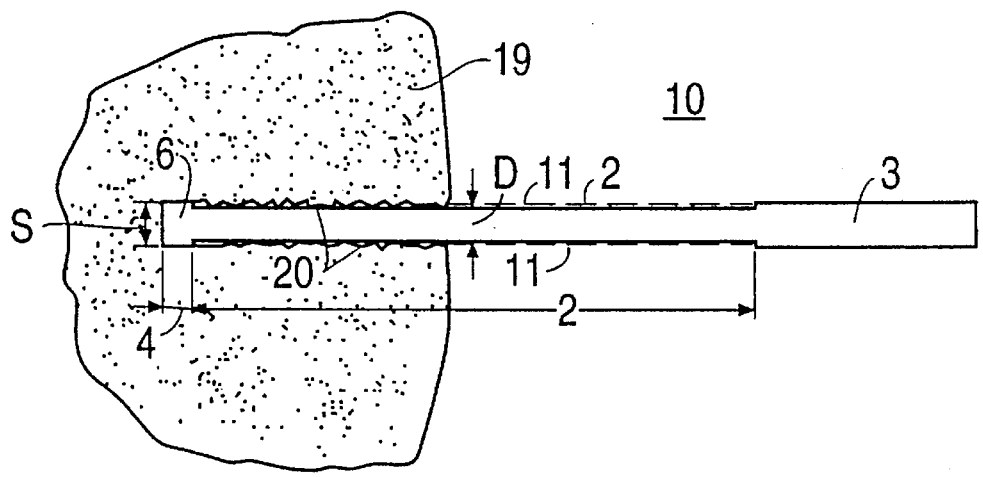

SAW BLADE FOR PARTING CUTS MADE IN AN OSCILLATING OR ROTARY MANNER

FIELD OF THE INVENTION

The invention relates to a saw blade for parting cuts performed in an oscillating or rotary manner with a cutting area, a non-cutting blade area and a holding area, particularly with saw-teeth as the cutting area and for use in bone surgery, as well as to a production process.

BACKGROUND OF THE INVENTION

Such saw blades, or put more generally also blade-like parting or cutting tools with a peripherally cutting chip area, are used e.g. in the medical field, as well as in precision mechanics, aircraft construction, ship building, microelectronics and for cutting composite materials. For the particularly demanding and delicate use in bone surgery e.g. microsaws with teeth set to the left and right or further developments with no such offset teeth arrangement are known from German patent 32 22 339. However, these known cutting tools suffer from significant disadvantages. They are generally small tools for precision working, which are e.g. manufacturable by etching or laser technology. A particularly simple and rational manufacture of saw blades by etching leads to the formation of pores and unevennesses on the surface. A surface which is uneven and has pores is very disadvantageous for surgical applications, where working has to take place in a completely sterile manner, because bacteria and germs can be deposited in the unevennesses, which makes the necessary sterilization very difficult. A further disadvantage is the lack of slidability on the part of known saw blades. It is very important in the case of demanding parting cuts in delicate materials and in particular in bone surgery to reduce the friction on the material and therefore produce a minimum of heating in sensitive bone material, so as to prevent thermonecrosis. For this purpose it is necessary to detect at an early stage any wear and therefore blunting of the cutting tool.

SUMMARY OF THE INVENTION

An object of the present invention is to provide a cutting tool or saw blade, which overcomes the aforementioned disadvantages and in particular leads to reduced friction and heating of the severed material.

According to the invention, a relatively soft precious metal coating leads to a smoothed surface with a slight lubricating action, so that the friction in particular in the bone tissue is greatly reduced. As a result of the reduced blade thickness in the relatively large non-cutting area, the friction of the saw blade on the severed material is greatly reduced, making it possible and appropriate for the first time to use a soft coating. A soft surface coating on the cutting, hard part of the toothed area would become immediately abraded and therefore pointless. However, as comparatively speaking the non-cutting area has a very large surface and the cutting tooth area is very small, the friction reduction by the soft precious metal coating on said large surface in accordance with the invention leads to a significant reduction of the overall friction when sawing and therefore also to a correspondingly reduced heating of e.g. sensitive bone material. In addition, through the use of a biologically neutral or body-compatible precious metal it is made possible to produce and allow a minimum abrasion of the coating acting in a lubricating manner, because this does not give rise to any harmful consequences in the bones and the body of the patient.

The coating according to the invention is completely the opposite of the hitherto known coatings, e.g. using chromium, which are chosen as hard as possible and where absolutely no abrasion is allowed. In the case of the known hard metal coatings, such as with chromium, there is also a much greater risk of said materials flaking off during sawing due to stressing during sterilization processes. Small fragments of such hard coatings left behind in the case of a bone cut can have a very negative effect in the healing process.

Other features of the invention relate to advantageous further developments with particularly appropriate saw blade shapes, materials in very thin coatings and films and rational production processes, which further increase the cutting action and reduce heating. In order to be able to detect in a completely satisfactory manner traces of wear, the surface coating can be optically clearly distinguished from the blade substrate material and is advantageously made matt. A pure gold coating, which is also advantageous for other reasons, makes it possible to readily distinguish signs of wear and therefore also the blunting of the cutting tool.

With a pure gold coating according to the invention pores and unevennesses of the base material are smoothed and levelled, so as to produce a homogeneous, readily adhering surface coating with high sliding characteristics. A gold coating in the case of special steel types, such as high-power, high-speed steel, has the advantage of preventing oxidation, making it possible for the first time to use in a completely sterile manner such hard steels.

A readily visible, e.g. gold, very thin precious metal coating for surgical saw blades reveals traces of wear in the coating through contact with the bone to be severed, so that from the number and intensity of such wear traces the surgeon is informed that the particular saw blade should be no longer used, because it has become blunt and also fails to satisfy sterility requirements. This also prevents, either unintentionally or for economy reasons, patients from being treated with a no longer completely satisfactory tool. Working with a blunt tool leads to the risk of an increased cutting pressure being exerted, which leads to the formation of high friction heat levels. When used in surgery such friction heat leads to thermonecroses, i.e. cell death of the bone tissue, which is one of the most feared complications following bone surgery. The problem is that when working the surgeon can neither see nor feel whether he has caused damage, which only becomes subsequently apparent. Even in the case of microscopic examination it is also not possible for the surgeon or instrument sister to optically establish whether a saw blade is blunt. Due to the uncontrollability of the cutting edge sharpness and inadequate cutting characteristics, there has been a marked increase in thermonecroses of late. In addition, the bone can also splinter by working with a blunt blade, or the breaking of the saw blade can lead to parts thereof being left behind in the bone. Disadvantages of a similar nature generally occur when mechanically working or machining workpieces with blunt or non-optimum tools, because the material being worked becomes too hot and is therefore damaged. This can e.g. make difficult or even impossible the working of plastic composite materials.

When using a saw blade or a cutting tool in surgery it is vital that the material used and which comes into contact with the living body during an operation, does not lead to immune reactions of the living body or cause other harmful interactions.

Further details and advantages of the invention can be gathered from the following description of exemplified embodiments of saw blades with reference to the attached drawings, wherein:

BRIEF DESCRIPTION OF THE DRAWINGS

FIG. 1 is a schematic side elevation of a surgical saw blade according to the invention for a linearly oscillating cutting movement.

FIGS. 2a and 2b are an edge view and a partial side view, respectively, of a saw blade for oscillating movement along a circular arc path.

FIG. 3 is a side elevation of the full blade a portion of which is shown in FIG. 2.

FIG. 4 is a side elevation similar to FIG. 3 showing abrasion tracks in the precious metal coating.

FIG. 5 is a schematic edge view of a saw blade severing a bone.

DESCRIPTION OF THE PREFERRED EMBODIMENTS

Figure 6:
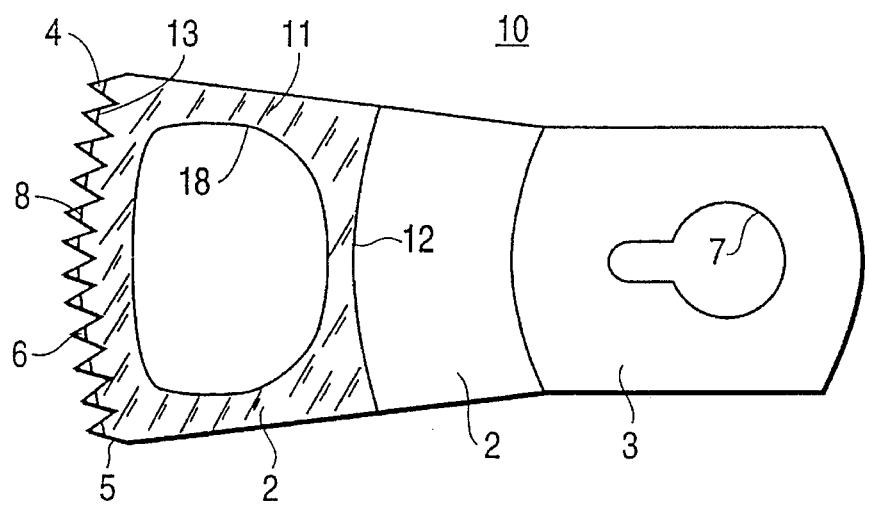
FIG. 6 is a side elevation of a saw blade with recesses.

The micro saw blade 1 shown in FIG. 1 has a cutting area 4 and a holding area 3 with a recess 7 integrally connected thereto and which is used for fixing the saw blade to a drive unit and for giving a substantially linearly oscillating movement 21 thereto. As in the example of FIGS. 2a and 2b, the saw blade has non-offset saw teeth 5, the cutting area 4 bounded by the line 8 only being formed by the tooth crests 6 in the form of cutting triangles. The tooth crests in the cutting area 4 have a greater thickness S1 corresponding to the width of cut S than the following, non-cutting blade area 2 with the thickness D. The non-cutting blade area 2, including the lower tooth area, is thinly coated on both sides and up to the boundary line 13 with a precious metal coating, preferably gold or platinum. FIGS. 2a, 2b and 3 show as a whole and in partial views from the side and top as a further example a saw blade 10 for oscillating cutting or parting movements substantially on a circular arc portion, e.g. for femoral neck cuts in surgery. The movement of the cutting area 4 of the teeth 5 has a main component 22 in the tangential direction with an amplitude of e.g. 1 to 3 tooth spacings and a much smaller vertical component 23 in the radial direction. As can be gathered from FIG. 2a, the holding part 3 and the cutting part 6 of the teeth, which is bounded by the line 8, has a greater material thickness S1 of e.g. 0.35 mm, whereas the following, non-cutting blade area 2 has a smaller material thickness D of e.g. only 0.25 mm. In this case the precious metal coating 11 covers on both sides the entire non-cutting blade area 2, defined by the line 13 and which here corresponds to the cutting boundary 8 and towards the holding area by the boundary line 12. Preferably the cutting triangles of the tooth crests 6 only take up approximately 30 to 50% of the tooth height, which in the case of a tooth height of e.g. 1 mm gives a cutting triangle height of 0.3 to 0.5 mm. In surgery, it is possible to achieve very fine separating or parting cuts with such micro saw blades with very high frequencies of e.g. 20,000 to 60,000 strokes/minute with a very small amplitude. However, with the high frequencies the friction and hating also increase, so that the friction-reducing construction according to the invention with the precious metal surface coating permits particularly fine, careful and precise cuts.

Figure 7:
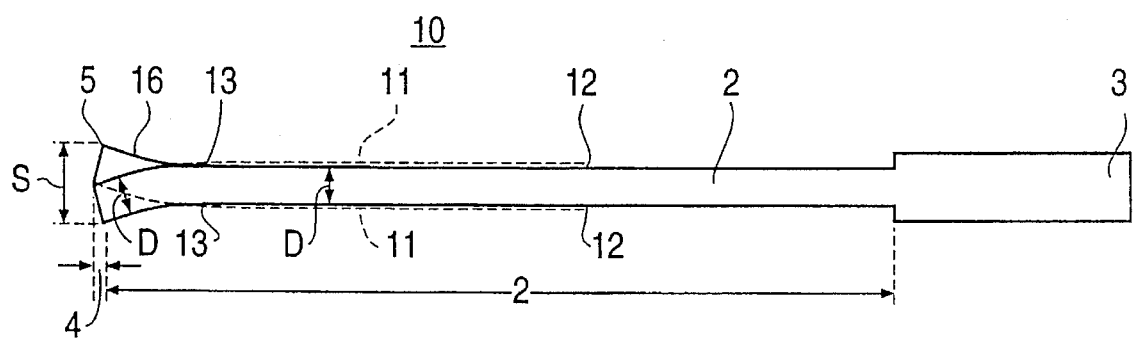
FIG. 7 is a schematic top plan view of a saw blade with teeth set to the left and right.

FIG. 7 shows a saw blade with teeth 16 set to the right and left and which have the same thickness D as the non-cutting blade area 2. The width of cut S is produced by the teeth located alternately on one or other side. Although such saw blades have clearly inferior parting characteristics to those with non-offset teeth in accordance with FIGS. 1, 2 and 8, even here it is possible to improve the sliding characteristics and therefore the parting action by means of the surface coating according to the invention. FIG. 4 shows the saw blade of FIGS. 2 and 3 after use. In the thinner, non-cutting blade area 2 the precious metal coating 11 is zonally removed in streaked manner with abrasion tracks 24, illustrating that the saw blade must be no longer used due to bluntness.

The function of the saw blade is further illustrated by FIG. 5, which shows a bone 19 during the cutting process with a non-offset saw blade 10. The severed, relatively large bone cut faces 20 on either side of the saw blade unavoidably rub on the non-cutting blade area 2. As stated, this friction is reduced by the surface coating 11 and the reduced thickness D to a significant extent. Thus, the saw blade is less stressed, so that the blade breakage risk is reduced. In turn this makes it possible to use finer, more precise and gentle micro saw blades. FIG. 6 shows a saw blade with a recess 18 in the non-cutting area 2 close to the teeth 5, which further reduces friction.

Figure 8:
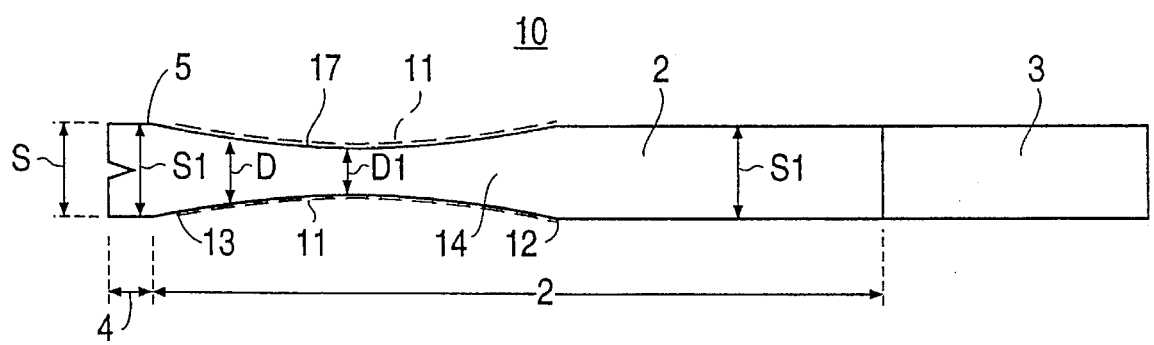
FIG. 8 is a schematic top plan view of a saw blade having reduced thickness in the non-cutting blade area.

FIG. 8 shows a further example of a non-offset saw blade having in the cutting area 4 and as from the line 12 in the blade area 2 and in the holding area 3, the same thickness S1, which corresponds to the width of cut S. Following on to the cutting area 4 said saw blade has a concave taper 17 with a thickness D reduced to a minimum value D1. Here, as in FIG. 7, the precious metal coating is not completely extended up to the cutting area 4 and instead ends before this at the boundary lines 13 and 12.

The saw blade can be shaped by laser or water jet cutting or also by conventional mechanical machining processes. A particularly rational process, e.g. for a saw blade according to fig. 2, is constituted by shaping by the removal of blade material 14 by etching and using a mask, which leaves open the non-cutting blade area 2 with the boundary lines 12, 13. The material thickness of S1 is reduced to D. Subsequently and using the same mask in the blade area 2 a thin gold surface coating 11 having a smoothing action is electrochemically or electrolytically applied. The precious metal coating is applied in thin form, e.g. by vacuum deposition and is preferably well below 1 μ, e.g. with an average coating thickness of 10 to 100 nm, which is also very cost effective. Advantageously the coating is matte, so as to avoid glare when operating.

The cutting tools according to the invention are particularly suitable for medical purposes, but they are also usable with similar advantages in other technical fields.

We claim:

1. A saw blade for making parting cuts when driven in an oscillating or rotary motion, the blade comprising a holding area comprising a blade substrate material;

a cutting area having saw teeth for making a cut having a width (S);

a non-cutting blade area having a thickness (D) in at least selected zones which is less than said cutting width (S) of said cutting area; and a surface coating (11) comprising a biological neutral precious metal on at least selected zones of opposite sides of said non-cutting blade area, said surface coating being softer than said blade substrate material, said cutting area being not covered by said surface coating.

2. A saw blade according to claim 1 wherein said surface coating is optically distinguishable from said blade substrate material.

3. A saw blade according to claim 1 wherein said saw teeth of said cutting area have a larger thickness (S1) than the thickness of said non-cutting blade area including said surface coating.

4. A saw blade according to claim 1 and comprising means defining a recess extending through said non-cutting blade area, said surface coating extending from adjacent said cutting area at least to said recess.

5. A saw blade according to claim 1 wherein said surface coating comprises a vacuum-deposited precious metal coating.

6. A saw blade according to claim 1 wherein said surface coating comprises an electrolytically applied precious metal coating.

7. A saw blade according to claim 1 wherein said surface coating has a matte finish.

8. A saw blade according to claim 1 wherein said surface coating has an average thickness of less than 1μ.

9. A saw blade according to claim 1 wherein the thickness of said surface coating is between 10 nm and 100 nm.

10. A saw blade according to claim 1 wherein said surface coating comprises gold.

11. A saw blade according to claim 1 wherein said surface coating comprises platinum.

12. A saw blade according to claim 1 wherein the thickness of said surface coating is selected so that, during use, abrasion of said coating becomes clearly visible when said cutting area begins to become blunt.

* * * * *